(12) United States Patent
Rice

(10) Patent No.: US 7,434,993 B2
(45) Date of Patent: Oct. 14, 2008

(54) RADIOGRAPHIC CASSETTE HOLDING DEVICE

(76) Inventor: Richard Calvin Rice, 8861 E. Neptune Dr., Flagstaff, AZ (US) 86004

( * ) Notice: Subject to any disclaimer, the term of this patent is extended or adjusted under 35 U.S.C. 154(b) by 0 days.

(21) Appl. No.: 11/670,704

(22) Filed: Feb. 2, 2007

(65) Prior Publication Data

US 2008/0025472 A1      Jan. 31, 2008

Related U.S. Application Data

(60) Provisional application No. 60/834,830, filed on Jul. 26, 2006.

(51) Int. Cl.
*G03B 42/04* (2006.01)
(52) U.S. Cl. ...................... 378/177; 378/167
(58) Field of Classification Search ................ 378/167, 378/170, 176, 177, 178, 180, 181, 184, 189
See application file for complete search history.

(56) References Cited

U.S. PATENT DOCUMENTS

| | | | |
|---|---|---|---|
| 4,468,803 A | 8/1984 | Ronci | |
| 4,691,333 A * | 9/1987 | Gabriele et al. | ............... 378/37 |
| 5,738,640 A * | 4/1998 | Carlson-Orsi | ................ 602/19 |
| 6,086,152 A * | 7/2000 | Zeller | ...................... 297/284.5 |
| 6,811,311 B2 | 11/2004 | Hayes et al. | |
| 6,931,782 B1 * | 8/2005 | Pitcock | ....................... 43/21.2 |
| 7,066,645 B2 | 6/2006 | Reid et al. | |
| 2003/0021383 A1 * | 1/2003 | Masson et al. | .............. 378/177 |
| 2006/0137071 A1 * | 6/2006 | Rampersad | ...................... 2/24 |

* cited by examiner

*Primary Examiner*—Hoon Song
(74) *Attorney, Agent, or Firm*—Jim Passé; Passé Intellectual Property, LLC

(57) ABSTRACT

The present invention relates to a device for supporting a radiographic cassette during the taking of an x-ray. The device as shown in FIG. 1 is especially useful to support a radiographic cassette for an x-ray of the patellofemoral joint utilizing an inferosuperior projection. The device consists of a counter balancing base unit and two straps each with attachment means to attach to the top of the radiographic cassette. When attached the device holds the cassette in position by counter balancing force.

4 Claims, 4 Drawing Sheets

RADIOGRAPHIC CASSETTE HOLDING DEVICE

This application claims priority of U.S. application Ser. No. 60/834,830 filed Jul. 26, 2006 and incorporated herein in its entirety by reference.

FIELD OF THE INVENTION

The present invention relates to an apparatus for supporting a radiographic (X-ray) cassette during the process of taking an X-ray. More particularly, it relates to a device for use to support a radiographic cassette for an x-ray of the patellofemoral joint utilizing an inferosuperior projection.

DESCRIPTION OF THE RELATED ART

In the practice of taking an x-ray, x-ray film is loaded into a radiographic cassette. It has generally been necessary to move the patient in differing positions to photograph the various anatomical parts. Since a patient having an x-ray generally should not be moved or is in need of immobilization, the current methods have some drawbacks. In addition to the movement of a patient being difficult and potentially harmful to the patient, it can be difficult for the health care worker, in addition to being laborious and time consuming.

A particular problem exists when taking an image of the patellofemoral joint. Currently, there is a method in use where the cassette holding the film is placed superior to the knee on the thigh and sandbags or a similar weighting device are leaned against the cassette on either side to hold the cassette in place in an upright position. Additionally, tape is used in an attempt to stabilize the cassette by having the patient hold the tape, taping the cassette to the table, taping the cassette to an area on the patient superior to the cassette or the like. An alternate method in use for the patellofemoral joint is to have an additional technologist, nurse or the like hold the cassette in place for the patient. A third method in use is to require the patient to sit upright and hold the cassette during the filming process. Each of the current methods has serious drawbacks and complications. Heavy weights on the patient can cause decreased circulation and even pain. Adding another person in the room means that a healthcare worker or other person is unnecessarily exposed to radiation. While sitting up solves some of those problems, sitting can be virtually impossible for patients that are heavily sedated, semi conscious or amputees. It can be extremely difficult for the morbidly obese, elderly, injured or patients with back problems. Also the sitting position exposes the patient's head, eyes, hands and thyroid gland to an increased dose of radiation compared to the patient in the supine position.

In fact, the holding of the cassette means that the hands might interfere with the image taking process. In fact, the supine position solves a great majority of the problems, however, very little alternatives are available and nothing has been designed specifically for the inferosuperior projection x-ray of the patellofemoral joint.

A great deal of work has been done in designing devices for holding radiographic cassettes in a fixed position during radiographic exposure. For example, a frame type device is shown in U.S. Pat. No. 6,811,311 to Hayes et al, which describes a combination patient support and a cassette holding means. In U.S. Pat. No. 7,066,645 to Reid et al, there is disclosed a holder designed for positioning underneath the patient. Lastly, in U.S. Pat. No. 4,468,803 to Ronci, there is a cassette holding suspension device with a series of 4 arms, multiple adjustment knobs and clamps for attaching to a table.

One solution for taking the x-ray of the patellofemoral joint with the patient in the supine position is to obtain a superoinferior projection of the joint using a Merchant board which attaches to a patient's legs after they have placed their legs over the edge of the x-ray table. This approach can be extremely uncomfortable especially for trauma and post operative knee patients. Also, Merchant boards can require the patient to rotate the legs through a frame-like apparatus causing additional trauma or pain to the patient.

While all these devices seem to have their uses, they do not address the serious problems associated with obtaining a patellofemoral radiograph. It would therefore be extremely useful to have a device which overcame one or more of the above described difficulties in taking a patellofemoral x-ray.

BRIEF SUMMARY OF THE INVENTION

The present invention relates to a device which overcomes many of the problems of the previous attempts at stabilizing a radiographic (x-ray) cassette for use in taking an x-ray of the patellofemoral joint. The invention eliminates the need for a second party to hold the cassette. The invention allows the patient to lie in a supine position and to stabilize the cassette perpendicular to the x-ray beam, and obtain a radiograph without causing blurring on the manifest image or exposing the patient to unnecessary additional radiation during the x-ray exposure. Additionally, it results in a radiograph of improved quality since it reduces the amount of "air gap" by effectively "extending" the patient's reach while in the supine position by approximately 6-8 inches. Air gap refers to the distance between the body part being x-rayed and the x-ray cassette. The greater the air gap, the greater the magnification of the part on the manifest x-ray image, as well as a loss of recorded detail. Because of the smaller air gap, the end result is a radiograph with less magnification and greater recorded detail.

In accordance with an embodiment of the invention, therefore, there is disclosed a device for positioning and supporting an x-ray cassette for taking an x-ray image of a patient's patellofemoral joint while the patient is in the supine position, the device comprising:
  a. an x-ray cassette counter-balancing base;
  b. two cassette attachment straps attached to the base and each having two strap ends; and
  c. at least one end of each of the cassette attachment straps having a detachable cassette attachment means and being attached to the base such that the device produces a counter-balancing force when it is attached to an x-ray cassette by the cassette attachment means.

These and other objects of the present invention will be clear when taken in view of the detailed specification and disclosure in conjunction with the appended figures.

DETAILED DESCRIPTION OF THE INVENTION

The general description of the x-ray cassette holder of the invention and how to use the device are stated in the Brief Summary above. This detailed description defines the meaning of the terms used herein and specifically describes embodiments in order for those skilled in the art to practice the invention. The above interests in successful taking of patellofemoral joint x-rays and more, as can readily be seen from the disclosure which follows, are met by the present invention. This detailed description defines the meaning of the terms used herein and specifically describes embodiments in order for those skilled in the art to practice the invention.

Figure 5:
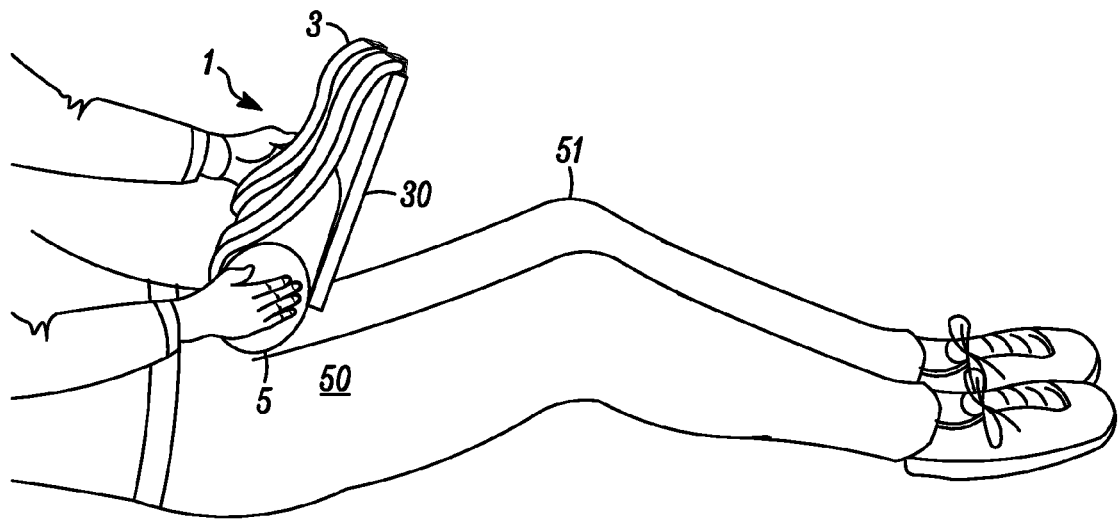
FIG. 5 is a perspective view of the device of the invention holding a radiographic cassette on a patient's legs in place for an x-ray.

As used herein a "counter-balancing base" refers to a base portion of the invention that can be attached to an x-ray cassette to stabilize it during taking of an x-ray. As to size and shape the base would be of a size that is about patient width or anywhere from 12 to about 24 inches wide. It would be from about 3 inches to about 12 inches in diameter. In one embodiment, the shape could be either a cylindrical, bolster style or the like. In another embodiment, it would have at least some portion of the base having a curved edge to facilitate the rolling of the base to adjust the position of the base. In yet another embodiment, it could be a rectangular shape or 3-sided. In another embodiment, contoured or shaped to fit the patient at the point of contact. In general, it will be a shape that would easily fit across the hip area of the patient, and handled as needed, as depicted in FIG. 5 to be described herein. The base can be made of any suitable material as long as it is not so heavy or uncomfortable so as not to be tolerated by the patient. So, for example, the base could be made of wood, plastic, metal, glass or the like. In another embodiment, the base is made of soft material such as cotton batting, polymer foam, pillow foam or the like. The base can optionally be covered with cloth, vinyl, Naugahyde, Scancoat, leather or the like. Where the base is covered, the seams of the cover can be sealed to prevent entry of water, bodily fluids and the like. This can be done by introducing a sealant to the seams or in the case of a cover like vinyl, the seams can be melted together or thermally sealed. The weight of the base can be such that it counter balances perfectly the weight of a selected cassette. This can be done by matching the weight of the base to the cassette or in other embodiments, a lighter than counterbalancing base is used and additional weights (such as sand bags or metal weights) are added to the base by means of Velcro, snaps or the like, to accomplish the desired balancing weight. This might be useful where the base material is a softer, pillow type material. In another embodiment, the design of the base and the length of the straps are such that the patient can hold the base from a supine position and thus provide the necessary counter balancing weight and still remain supine.

As used herein an "x-ray cassette" is essentially a rectangular plastic, metal or the like, light tight holder designed for containing a piece of radiographic film or other image receptor such as a laser read or digital imaging plate which are used in computed radiography and digital radiography for taking an x-ray and are well known in the art. The thickness of the standard cassette is roughly one half inch. For the patellofemoral joint, one cassette is usually about the width of the patient and the base of the device is about the same width as the cassette being used. For example, for a view of a single knee or "unilateral" exam, an 8×10 cassette would be appropriate, while for both knees simultaneously or a bilateral exam, an 11×14 or 14×17 cassette would be appropriate Clearly, the present invention can be adapted to accommodate any size cassette for this purpose based on the teachings herein.

As used herein "cassette attachment straps" are a length of cord, rope, strapping material, thread, wire or the like that can be used in pairs to attach the base to the x-ray cassette. For convenience herein, they will be called straps but one skilled in the art from the description and drawings herein will be able to substitute appropriate alternatives. They are an appropriate length to reach and stabilize the cassette but in one embodiment they are about 12 inches to about 36 inches in length. In one embodiment, the straps are made of a double layer of thermally sealed vinyl. Each strap will have two ends. In one embodiment, one end of each strap will attach to the base and one end will attach, detachably to a cassette. Note that in this embodiment both strap ends would attach to the same side of the cassette namely the top edge or top portion spaced to produce an even force on the cassette. In another embodiment, each of the ends can attach to a cassette, while a middle portion of each strap will attach to the base either permanently or detachably. In this configuration, two ends would attach to the top of the cassette and two to the bottom. This configuration has the advantage of stabilizing the bottom edge of the cassette from sliding on the patient. It should be noted that attachment can be by simply wrapping the straps around the base and friction holding them in place or the pull of a cassette against the base holding them in place. Any place where the straps are wrapped entirely around the base would work as an embodiment of the invention. The "detachable cassette attachment means" can be clips as shown in the drawings or other fasteners such as hook and loop fastener (e.g. Velcro), snaps, buttons or the like. The important characteristic of this attachment means is that the strap be attachable for use and removable from the cassette after the x-ray is taken. In one embodiment, the straps are adjustable in length. This feature would accommodate different sized cassettes, slightly different positioning on different sized patients and the like. An adjustable sized strap can be accomplished by placing hook and loop fasteners at each end in such a manner that the strap can be shortened or lengthened as needed to accommodate the cassette. Other methods of adjusting the strap can be used and are well known in the art. For example, a belt buckle, backpackers slide, snaps, or the like could be used to adjust the strap length.

When attaching the straps to the base at a middle portion or at one end, they can be attached removably or permanently attached. Removable attachment means could be hook and loop, snaps, buttons or the like. Permanent attachment to the base could be, for example, by sewing or gluing the strap to the base, or by means of a hook and loop system. In one embodiment the straps are thermally sealed to the base.

As used herein "counter-balancing force" means that the exact placement of the straps on the base when attached to a cassette as well as their length is designed to be such that the cassette will stay in place for a patellofemoral joint x-ray with little or no effort on the part of the patient when the device of the invention is in use. Where the base is weighted such that it perfectly counters the force of the cassette leaning during the taking of the x-ray, no effort is required by the patient. Where desired, the patient, while still in a supine position may extend one or two hands to grab the base, thus easily adding the necessary counter force to keep the cassette upright and in the proper position. In an alternative embodiment, a weight could be added to the base to produce the exact counter forces for each cassette the base was used to counterbalance. That way one device could be used with a number of different sized cassettes. The attachment means to the cassette, especially where there are four strap ends attached to the cassette, provide a force that prevents the end of the cassette in contact with the patient from slipping. Note that in use, the cassette would be placed for an inferosuperior projection of the patellofemoral joint on mid thighs and the base at about hip level. In attaching the straps to a cassette, at least two ends would be attached to a top portion of a cassette. Where 4 attachment means are used, two attachment means would be used on top, while two would be at the bottom of the cassette as well. It is clear that additional straps could be used in conjunction with the device, but the minimum number of straps for the invention is two.

In the use of the device of the invention, the patient lies in the supine position with their feet placed nearly flat on the exam table. The patient bends their knees to approximately 30 to 45 degrees. The device of the invention is attached to the x-ray cassette as described above and the device base portion is placed on the patient's abdomen, proximal femur or the like depending on the body shape and size and other factors necessary to position the cassette correctly for an x-ray. The base is turned or rolled either toward or away from the cassette such that it causes the straps to be drawn around it until the base rests against the back of the cassette acting as a stabilizer. To produce an image of diagnostic quality, the cassette must be perpendicular to the x-ray beam. This is accomplished by tilting the base portion of the device backwards or forwards, along with the cassette, to increase or decrease the angle of the cassette until it is perpendicular to the x-ray beam.

When a counterbalancing weight is attached to the base as described and claimed herein, it can be a sand bag, iron weight, buck shot bag or the like which can be removably attached to the device base as necessary to counter the weight of the cassette. One skilled in the art could easily figure the right size weight and placement of the weight to achieve such counterbalancing force by an added weight.

Figure 1:
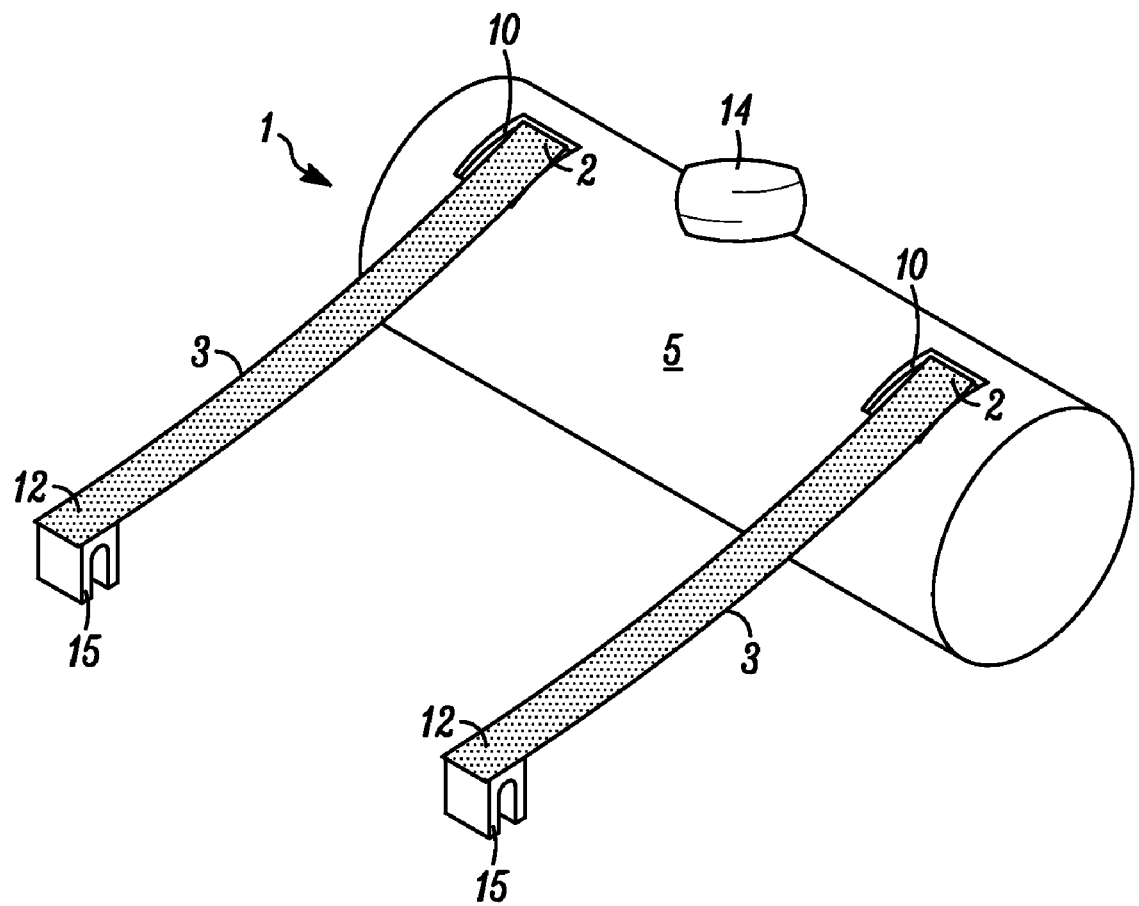
FIG. 1 shows a perspective view of an embodiment of the Invention showing 2 cassette attachment means.

Now referring to the drawings, FIG. 1 depicts a perspective view of an embodiment of the cassette holding device 1 wherein the first end of each strap is attached directly to base 5. In this embodiment, strap 3 is removably attached to base 5 by attachment to hook and loop patch 10. Base 5 in this view is cylindrical in shape and can easily be rolled during use as described above. At second strap end 12, is clip cassette attachment means 15. Clip cassette attachment means 15 is designed for attaching to the top portion of a cassette. Also, depicted is optional counterbalancing weight 14, shown in this embodiment as a sand bag.

Figure 2:
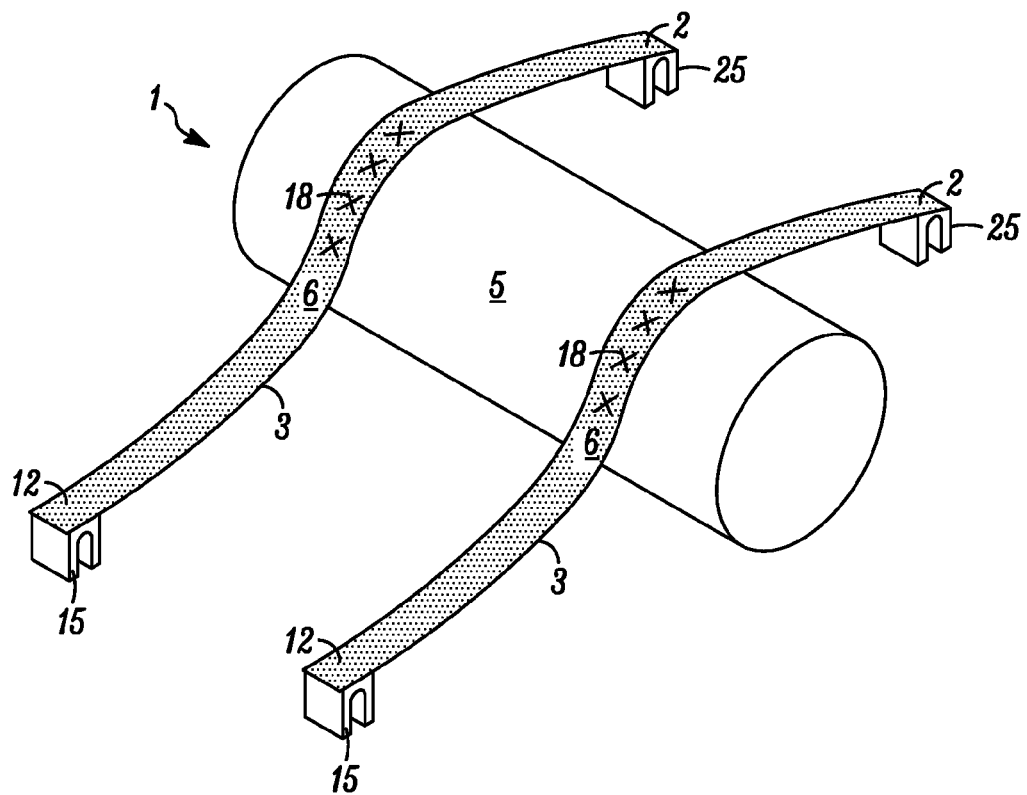
FIG. 2 shows a perspective view of an embodiment of the invention showing 4 cassette attachment means.

Depicted in FIG. 2 is an alternate embodiment of the cassette holding device 1 of the invention where the straps 3 are attached in a middle portion 6 of each strap to the base 5. In addition, in this embodiment strap 3 has at first end 2, a cassette attachment means 25 designed for attaching to the bottom edge of an X-ray cassette. Also, in this embodiment the straps 3 are attached to base 5 via thermal sealing 18 of the strap 3 to the base 3. Cassette attachment clips 15 for attaching to the top of the cassette are also shown in this embodiment. The straps in this figure in another embodiment could of course be attached via any of the methods listed herein or via those methods known in the art. Likewise, the straps may be held in place merely by wrapping them around the base and the weight of the cassette holding the straps against the base. In one embodiment, the straps 3 are adjustable in length to accommodate various size cassettes.

Figure 3:
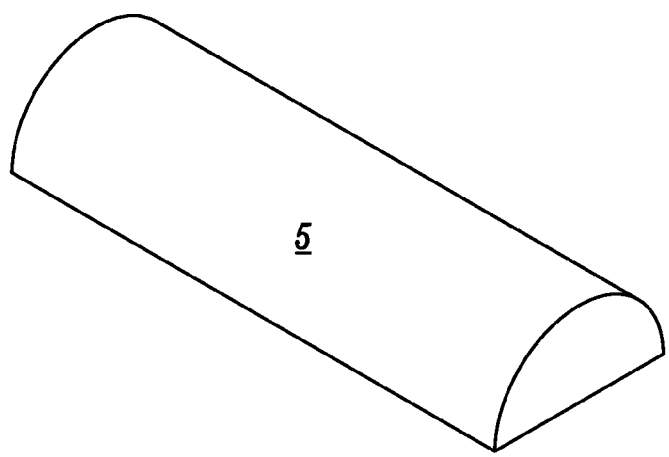
FIG. 3 shows an embodiment of the base wherein the shape is a bolster.

FIG. 3 depicts another embodiment of a base 5, which takes on a half cylinder or bolster shape. The pillow base 5 of FIG. 3 can be rolled on the curved side of the base.

Figure 4:
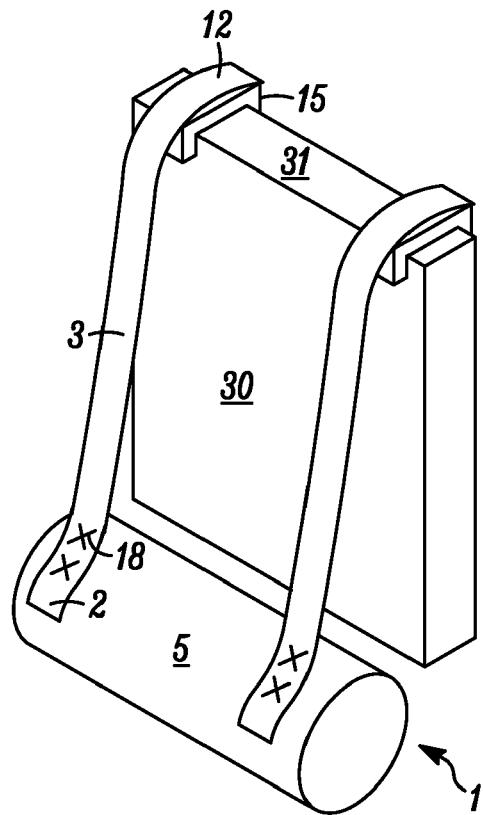
FIG. 4 depicts perspective views of 2 embodiments of the invention attached to a radiographic cassette where there are 2 and 4 cassette attachment means respectively.
Figure 4:
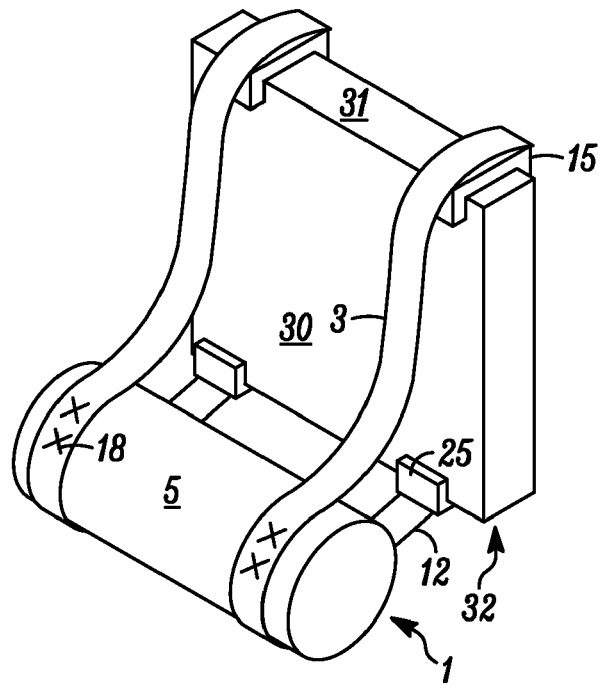

FIG. 4 depicts two embodiments of the invention as depicted in FIGS. 1 and 2, this time where each is attached to an x-ray cassette 30. In the top embodiment, Cassette 30 has top edge 31 where cassette attachment clips 15 of straps 3 have been attached. In the bottom embodiment, corresponding to FIG. 2, not only are cassette attachment clips 15 attached to top edge 31 as in the top embodiment, but the second cassette attachment means 25 are shown attached to the bottom edge 32 of cassette 30. The straps 3 in one embodiment are adjustable in length.

FIG. 5 shows the top embodiment of FIG. 4 in use with a patient 50. As can be seen from this embodiment the patient 50 is holding the base 5 to provide the remaining necessary counterbalancing weight to keep cassette 30 balanced and leaning toward the patellofemoral joint 51. While it is shown with the patient having both hands on the base, on can easily see that one hand will do the job by placement towards the middle of the base much as a counter balancing weight attachment would be positioned. The patient also has the base up against the cassette which helps in positioning the cassette and in some instances may be necessary to do. One skilled in the art could easily determine that need based on the disclosure herein. This embodiment may not be practical for some patients such as an unconscious patient or with certain types of injuries and thus the counterbalancing weight approach might be more appropriate for those patients. The flexibility of this invention along with the skill of those in the art will allow the user of the device to adapt its use according to the patients the cassette and the needs of the x-ray.

Figure 6:
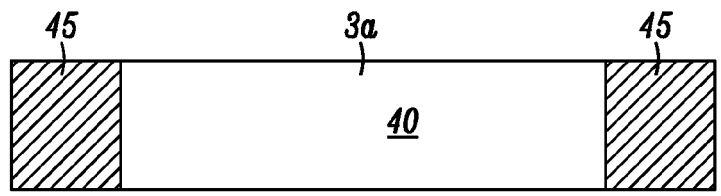
FIG. 6 is an overhead view of the top and bottom of two adjustable straps of the invention.
Figure 6:
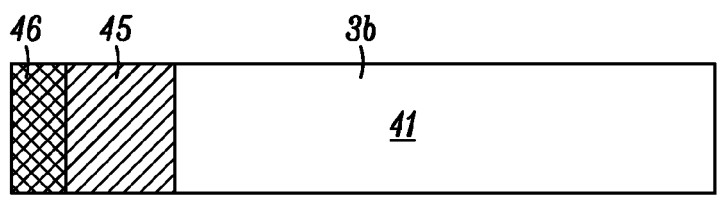

In FIG. 6 there is depicted an embodiment of the invention comprising two adjustable straps 3 of the invention. In this embodiment the top strap 3a is bottom side 40 up and the bottom strap 3b is top side 41 up. Depicted are loop fasteners 45 and hook fasteners 46. The bottom side 4 of loop fasteners 45 are used to attach to the base or a cassette to which hook fasteners are also attached. Top side 41 is fitted with a hook and loop length adjustment means. Hook fasteners 46 can be folded over to meet loop fastener 45 positioned on the top side 41 of each strap 3. In this way the length of the strap can be adjust a few inches to accommodate the cassette positioning. In one embodiment the strap 3 is about 2 inches wide and about 27 inches in length. In another embodiment, the top side 41 loop fastener 45 is about 3 inches and length and the hook fastener 26 about 1 inch in length. This last embodiment would give a length adjustment of about 3 to 4 inches in length.

The advantages of the present invention, as well as certain modifications of the disclosed embodiments, will be readily apparent to those skilled in the art. Since changes may be made in the foregoing device without departing from the scope of the invention herein, it is intended that all matter in the above invention embodiments and provided in the drawings shall be considered illustrative only and not considered limiting.

What I claim is:

1. A method for taking an x-ray image of a patient's patellofemoral joint, utilizing an inferosuperior projection, while the patient is in a supine position comprising:
    a) selecting an x-ray cassette;
    b) attaching a counter-balancing base to the top of the cassette with two cassette attachment straps attached to the base and to a top of the x-ray cassette;
    c) positioning the cassette for taking the x-ray;
    d) positioning the base in the patient's hip area;
    e) turning the base such that it causes the straps to be drawn around the base until the base rests against the back of the cassette and stabilizes the cassette position; and
    f) taking the x-ray.

2. A device for positioning and supporting an x-ray cassette for taking an x-ray image of a patient's patellofemoral joint, utilizing an inferosuperior projection, while the patient is in a supine position, the device comprising:

a) an x-ray cassette counter-balancing base designed to fit in the hip area of the patient;
b) an x-ray cassette; and
c) two cassette attachment straps attached to the base, each strap having at least two strap ends having cassette attachment clips for removably
d) wherein the length of the straps is that when the clips are attached to an x-ray cassette and the base is positioned in a hip area of the patient, the straps hold the x-ray cassette in a proper upright position for the taking of an x-ray of the patient's patellofemoral joint utilizing an inferosuperior projection.

3. A device according to claim 2 wherein the straps are adjustable in length.

4. A device according to claim 2 wherein the base has at least a portion of the base that is cylindrical.

* * * * *